(12) United States Patent
Bergeron et al.

(10) Patent No.: US 9,433,578 B2
(45) Date of Patent: Sep. 6, 2016

(54) STABLE BUBBLES VIA PARTICLE ABSORPTION BY ELECTROSTATIC INTERACTION

(71) Applicant: L'OREAL, Paris (FR)

(72) Inventors: Vance Bergeron, Francheville (FR); Jean-Thierry Simonnet, Mamaroneck, NY (US); Florence Levy, Paris (FR); Aurelie Lafuma, Paris (FR); Stephane Santucci, Lyons (FR)

(73) Assignee: L'OREAL, Paris (FR)

( * ) Notice: Subject to any disclaimer, the term of this patent is extended or adjusted under 35 U.S.C. 154(b) by 166 days.

(21) Appl. No.: 13/896,666

(22) Filed: May 17, 2013

(65) Prior Publication Data

US 2014/0341955 A1 Nov. 20, 2014

(51) Int. Cl.
| | |
|---|---|
| *A61K 9/12* | (2006.01) |
| *A61K 9/107* | (2006.01) |
| *A23L 1/00* | (2006.01) |
| *B01F 17/00* | (2006.01) |
| *A23L 1/48* | (2006.01) |
| *A23L 1/035* | (2006.01) |
| *A61K 8/25* | (2006.01) |
| *A61K 8/41* | (2006.01) |
| *A61K 8/02* | (2006.01) |
| *A61K 8/04* | (2006.01) |
| *A61K 8/19* | (2006.01) |

(52) U.S. Cl.
CPC .............. *A61K 9/107* (2013.01); *A23L 1/0097* (2013.01); *A23L 1/035* (2013.01); *A23L 1/483* (2013.01); *A61K 8/025* (2013.01); *A61K 8/0245* (2013.01); *A61K 8/0254* (2013.01); *A61K 8/04* (2013.01); *A61K 8/046* (2013.01); *A61K 8/19* (2013.01); *A61K 8/25* (2013.01); *A61K 8/416* (2013.01); *B01F 17/0007* (2013.01); *B01F 17/0042* (2013.01); *A61K 2800/596* (2013.01); *A61K 2800/805* (2013.01)

(58) Field of Classification Search
CPC ........ A61K 9/107; A61K 8/60; A61K 8/044; A61K 8/046
See application file for complete search history.

(56) References Cited

U.S. PATENT DOCUMENTS

| | | | |
|---|---|---|---|
| 3,661,602 A | 5/1972 | Gerow | |
| 3,725,095 A | 4/1973 | Weidman et al. | |
| 5,900,394 A | 5/1999 | Goel et al. | |
| 6,107,358 A | 8/2000 | Harada et al. | |
| 6,159,453 A | 12/2000 | Avnir et al. | |
| 6,238,650 B1 | 5/2001 | Lapidot et al. | |
| 6,248,315 B1 | 6/2001 | Young et al. | |
| 6,620,407 B1 | 9/2003 | Gers-Barlag et al. | |
| 6,677,389 B2 | 1/2004 | Fukuda et al. | |
| 7,670,999 B2 * | 3/2010 | Sebillotte-Arnaud et al. .................. 510/130 | |
| 2002/0192180 A1 | 12/2002 | Fairley et al. | |
| 2004/0241120 A1 | 12/2004 | Pataut et al. | |
| 2007/0258933 A1 | 11/2007 | Bui et al. | |
| 2007/0258934 A1 | 11/2007 | Bui et al. | |
| 2007/0275257 A1 | 11/2007 | Muraguchi et al. | |
| 2007/0292676 A1 | 12/2007 | Naigertsik et al. | |
| 2008/0199526 A1 | 8/2008 | Poschalko et al. | |
| 2009/0325780 A1 | 12/2009 | Gauckler et al. | |
| 2011/0158923 A1 | 6/2011 | Galeone et al. | |
| 2011/0293677 A1 | 12/2011 | Bekemeier et al. | |
| 2011/0311723 A1 | 12/2011 | Bekemeier et al. | |

FOREIGN PATENT DOCUMENTS

| | | | |
|---|---|---|---|
| DE | 19834819 A1 | 2/2000 | |
| EP | 0 107 199 | 5/1984 | |
| EP | 1038573 A2 | 9/2000 | |
| EP | 1627668 A1 | 2/2006 | |
| EP | 1759690 A2 | 3/2007 | |
| EP | 2436452 A1 * | 9/2010 | ............... B05B 7/00 |
| GB | 2 131 820 | 6/1984 | |
| JP | S627632 A | 1/1987 | |
| JP | S62164617 A | 7/1987 | |
| JP | 2004002275 A | 1/2004 | |
| JP | 2005-145876 A | 6/2005 | |
| WO | 94/00508 | 1/1994 | |
| WO | 96/14145 | 5/1995 | |
| WO | 2014184658 A2 | 11/2014 | |
| WO | 2014184659 A2 | 11/2014 | |
| WO | 2014184660 A2 | 11/2014 | |

OTHER PUBLICATIONS

Lomax, Ed. Amphoteric Surfactants Second Edition Marcel Dekker, Inc.; NY 1996, p. 121.*
Velikov et al. Langmuir 1998, 14, 1148-1155.*
Binks B.P., et al., "Enhanced Stabilization of Emulsions Due to Surfactant-Induced Nanoparticle Flocculation," Langmuir, 2007, vol. No. 23 (14), pp. 7436-7439.
Binks B.P., et al., "Synergistic Interaction in Emulsions Stabilized by a Mixture of Silica Nanoparticles and Cationic Surfactant," Langmuir, 2007, vol. No. 23 (7), pp. 3626-3636.
Dickinson et al., "Food emulsions and foams Stabilization by particles," Current Opinion in Colloid and Interface Science, London, GB, XP026896477, vol. 15, No. 1-2, (Apr. 1, 2010), pp. 40-49.
Hunter et al., "The role of particles in stabilising foams and emulsions," Advances in Colloid and Interface Science, Elsevier, NL, XP 022510900, vol. 137, No. 2, (Mar. 4, 2008), pp. 57-81.

(Continued)

*Primary Examiner* — Abigail Fisher
*Assistant Examiner* — Jessica Kassa
(74) *Attorney, Agent, or Firm* — The Marbury Law Group, PLLC

(57) ABSTRACT

Disclosed are methods of preparing stable gas-in-solution emulsions by particle adsorption via electrostatic interaction, and stable emulsions prepared by particle adsorption via electrostatic interaction. Compositions and products comprising the emulsions are also disclosed. Emulsions may be stable over an extended period of time at room temperature.

21 Claims, 4 Drawing Sheets

(56) References Cited

OTHER PUBLICATIONS

International Search Report for Application No. PCT/IB2014/001467, mailed Jan. 26, 2015, 3 pages.
International Search Report for Application No. PCT/IB2014/001485, mailed Nov. 25, 2014, 4 pages.
International Search Report for Application No. PCT/IB2014/001487, mailed Jan. 7, 2015, 4 pages.
Kaptay, G., "Interfacial Criteria for Stabilizing of Liquid Foams by Solid Particles," Colloids and Surfaces, A. Physicachemical and Engineering Aspects, Elsevier, Amsterdam, NL, XP008068726, vol. 230, No. 1-3, (Jan. 1, 2004), pp. 67-80.
Stamkulov, N. SH et al., "Stabilisation of emulsions by using a comgination of an oil soluble ionic surfactant and water soluble polyelectrolytes. I: Emulsion stabilisation and Interfacial tension measurments," Colloids and Surfaces, A. Physicachemical and Engineering Aspects, Elsevier, Amsterdam, NL, XP026654191, vol. 335, No. 1-3, (Mar. 5, 2009), pp. 103-106.
Stocco, Antonio et al., "Particle-stabilised foams: an interfacial study," Soft Matter, XP055163020, vol. 5, No. 11 (Jan. 1, 2009), pp. 2215-2222.
Wang, J. et al., "Synergistic stabilization of emulsions by poly(oxypropylene)diamine and Laponite particles," Colloids and Surfaces, A, Physicachemical and Engineering Aspects, Elsevier, Amsterdam, NL, vol. 353, No. 2-3, XP026806479, (Jan. 15, 2010), pp. 117-124.
Whitby, C.P. et al., "Effect of oil soluble surfactant in emulsions stabilised by clay particles," Journal of Colloid and Interface Science, Academic Press, NY, NY, vol. 323, No. 2, (Jul. 15, 2008), pp. 411-416.
International Preliminary Report on Patentability for PCT/IB2014/001485 (Nov. 26, 2015).
International Preliminary Report on Patentability for PCT/IB2014/001487 (Nov. 26, 2015).
International Preliminary Report on Patentability for PCT/IB2014/001467 (Nov. 26, 2015).
Falcone, "The Effect of Degree of Polymerization of Silicates on Their Interactions with Cations in Solution"; In Soluble Silicates; ACS Symposium Series; American Chemical Society; 1982; 16 pages.
Pub Chem "Sodium Meta Siliciate"; accessed Sep. 21, 2015; 32 pages.

\* cited by examiner

STABLE BUBBLES VIA PARTICLE ADSORPTION BY ELECTROSTATIC INTERACTION

FIELD OF THE DISCLOSURE

The disclosure relates to dispersions useful in a variety of applications, and methods for preparing the dispersions. The dispersions according to the disclosure may exhibit improved stability over an extended period of time, such as for several months, even when stored at room temperature.

BACKGROUND

Products in the form of aerated dispersions (e.g. gas-in-solution dispersions) are known, such as, for example, foams such as mousse products for styling the hair, as well as whipped cream and other food products that are dispensible from an aerosol can. Such products, however, are known to have poor stability, in particular at room temperature. For example, as can be seen in FIG. 1, an aerated dispersion can evolve over time, with gas bubbles growing and causing the dispersion to degrade.

Past attempts to formulate stable products have had the drawback that the product is affected by the addition of surfactants, polymers, and changes in temperature and/or pH. Other past methods for preparing and stabilizing formulated products utilize components that are toxic and/or produce by-products that can present health hazards and/or introduce prohibitive cost constraints to remove or neutralize them. Additionally, some aerated products are proposed in aerosol cans that simultaneously inject gas and solution, or that must be prepared and kept under frozen conditions to remain stable.

Further problems with the current methods for generating aerated products with particles at the gas-solution interface is that they concern foams and not gas-phase dispersions—that is, the systems have gas-phase volume fractions greater than 64%. In these systems the individual bubbles touch and stick together which makes it difficult to subsequently re-disperse the gas bubble into solution. Furthermore, only hydrophobic particles can be used to achieve even moderate stability.

US 2009/0325780 discloses stabilization of foams and emulsions using partially lyophobic and lyophilized particles. However, it is required to combine the particles in solution with amphiphilic molecules in order to make them hydrophobic before preparing the foam or emulsion. The resulting interfacial adhesion of particles to the surface of the gas bubble, however, is discrete, and somewhat discontinuous, as seen in FIGS. 2 and 3.

In addition to avoiding the above-mentioned drawbacks, there is also a desire in certain industries, such as, for example, the food, cosmetic, and consumer chemical (e.g. household product) industries, to prepare products that have certain properties, such as the ability to be further diluted, for instance.

Thus, there remains a need for methods to prepare gas-in-solution dispersions that provide the desired properties and which can be used in a variety of applications and industries, while providing increased stability of the dispersion and the formulated product.

SUMMARY

It has been discovered that gas-in-solution dispersions prepared via particle adsorption by electrostatic interaction allow for the formation of a rigid interface between the gas bubble and the continuous solution phase. The bubbles can be individually encapsulated, which may prevent coalescence or so-called Oswald-ripening, resulting in increased stability.

According to various embodiments of the disclosure, gas-in-solution dispersions can be prepared where the dispersed phase comprises gas bubbles, and the continuous phase comprises a surface-active material, by any method known. The surface-active material can be chosen to impart a charge at the interface of the gas bubble and solution. Subsequently, particles having the opposite charge to that of the surface-active material can be added to the continuous phase. This process leads to encapsulation of the gas bubbles, and gas-in-solution emulsions having improved stability over extended periods of time.

DESCRIPTION OF EXEMPLARY EMBODIMENTS

Figure 1:
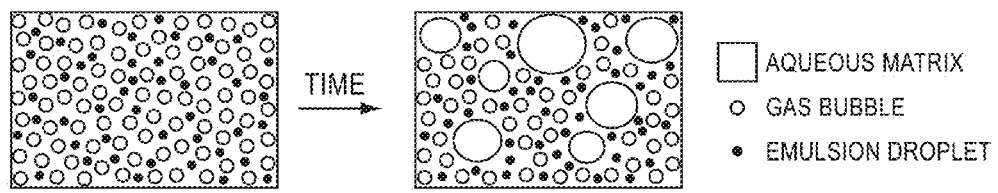
FIG. 1 is a diagram showing how known aerated dispersions can degrade over time.
Figure 2:
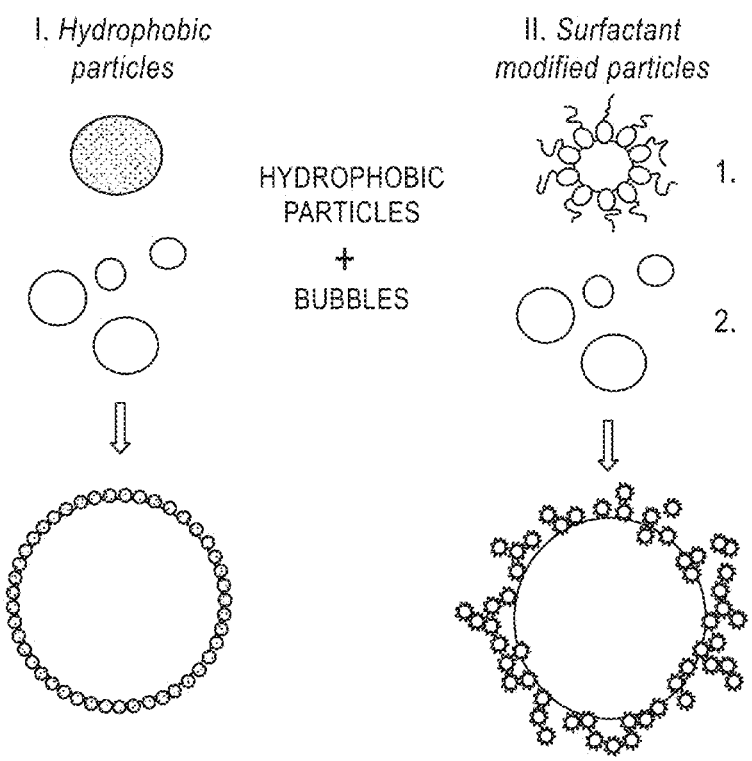
FIG. 2 a schematic of a prior art encapsulation process.
Figure 3:
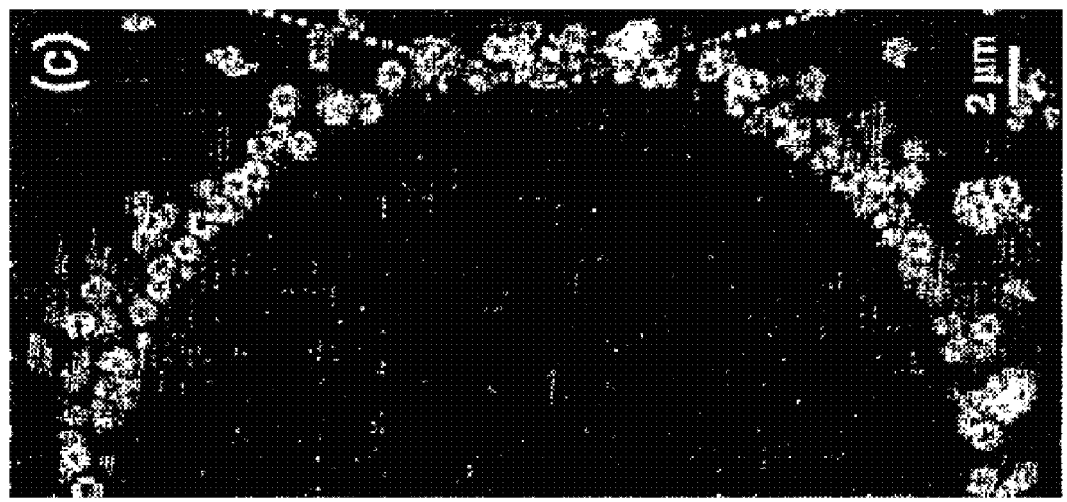
FIG. 3 is an image of a gas bubble with discrete particle coverage, prepared according to a prior art process.

The disclosure relates to gas-in-solution emulsions prepared via particle adsorption by electrostatic interaction, and methods of preparing such emulsions.

The encapsulation process may, in various embodiments, comprise steps of preparing a gas-in-solution dispersion, where the dispersed phase comprises gas bubbles and the continuous phase comprises a surface-active material at the bubble-solution interface. This may be done by any method known, such as, for example, by high speed blender (e.g. ultralux), rotor-stator, high pressure homogenizer, static mixer, in-line mixer, etc.

According to various embodiments of the disclosure, the gas-in-solution dispersion comprises, for example, about 10% to about 60%, such as about 10% to about 50%, about 15% to about 50%, about 15% to about 40%, about 20% to about 60%, about 20% to about 50%, about 25% to about 50%, such as about 25% to about 45%, of the dispersed phase, in the form of bubbles.

The gas bubbles of the dispersed phase may, according to various embodiments, be in the range of micron-sized. For example, the bubbles may range up to about 1500 μm, such as up to about 1000 μm, up to about 750 μm, or up to about 500 μm. By way of non-limiting example only, the bubbles may range from about 5 μm to about 1500 μm, such as about 10 μm to about 1000 μm, about 5 μm to about 1000 μm, about 10 μm to about 1500 μm, about 10 μm to about 750 μm, about 10 μm to about 500 μm, about 50 μm to about 1000 μm, about 50 μm to about 750 μm, about 50 μm to about 500 μm, or about 50 μm to about 250 μm. In further embodiments, the bubbles may range from about 30 μm to about 250 μm, such as about 30 μm to about 100 μm or about 50 μm to about 100 μm.

Any gas that is useful in the intended application may be chosen. By way of non-limiting example only, the gas bubbles of the disperse phase may be chosen from bubbles of air, O2, N2, CO2, N2O, He, and combinations thereof.

The continuous phase may be aqueous, and may comprise at least one surface active agent, which may cover the gas bubbles at the gas-in-solution interface. By way of example only, the at least one surface active agent may be chosen from cationic surface active agents, amphoteric surface active agents, and or amphiphilic polymers. When the surface-active agent covers the gas bubble, it imparts a charge to the coated gas bubble. By way of example only, the coated bubble may have a charge greater than about 40 mV, such as greater than about 50 mV, greater than about 60 mV, greater than about 70 mV, greater than about 80 mV, greater than about 90 mV, or greater than about 100 mV.

The at least one surface active agent may be present in an amount ranging from about 0.5 to about 50 times the Critical Micellar Concentration ("CMC") of the emulsion, such as, for example, about 0.5 to about 40 times the CMC, about 1 to about 40 times the CMC, about 1 to about 25 times the CMC, or about 1 to about 15 times the CMC.

Exemplary, non-limiting cationic surface active agents include optionally polyoxyalkylenated primary, secondary and tertiary fatty amines, quaternary ammonium salts, and mixtures thereof.

Exemplary quaternary ammonium salts may be chosen from:
those of the general formula (I) below:

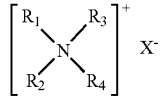

(I)

wherein R1, R2, R3, and R4, which may be identical or different, are chosen from linear and branched aliphatic radicals comprising from 1 to 30 carbon atoms, and aromatic radicals; and X— is chosen from halides, phosphates, acetates, lactates, (C2-C6) alkyl sulfates, and alkyl- or alkylaryl-sulfonates;
quaternary ammonium salts of imidazoline;
diquaternary ammonium salts of formula (II):

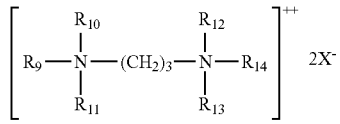

(II)

wherein R9 is chosen from aliphatic radicals comprising from 16 to 30 carbon atoms; R10, R11, R12, R13, and R14, which may be identical or different, are chosen from hydrogen and alkyl radicals comprising from 1 to 4 carbon atoms; and X— is chosen from halides, acetates, phosphates, nitrates, ethyl sulfates, and methyl sulfates; and
quaternary ammonium salts comprising at least one ester function.

Exemplary and non-limiting quaternary ammonium salts of imidazoline may be chosen from those of formula (III) below:

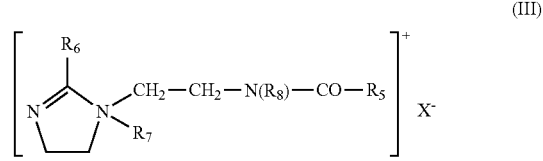

(III)

wherein R5 is chosen from alkenyl and alkyl radicals comprising from 8 to 30 carbon atoms; R6 is chosen from hydrogen, C1-C4 alkyl radicals, and alkenyl and alkyl radicals comprising from 8 to 30 carbon atoms; R7 is chosen from C1-C4 alkyl radicals; R8 is chosen from hydrogen and C1-C4 alkyl radicals; and X— is chosen from halides, phosphates, acetates, lactates, alkyl sulfates, alkyl sulfonates, and alkylaryl sulfonates.

By way of example only, the at least one cationic surfactant may be chosen from behenyltrimethylammonium chloride, cetyltrimethylammonium chloride, quaternium-83, quaternium-87, quaternium-22, behenylamidopropyl-2,3-dihydroxypropyldimethylammonium chloride, palmitylamidopropyltrimethylammonium chloride, stearamidopropyldimethylamine, and chloride and methyl sulfates of diacyloxyethyldimethylammonium, of diacyloxyethylhydroxyethylmethylammonium, of monoacyloxyethyldihydroxyethylmethylammonium, of triacyloxyethylmethylammonium, of monoacyloxyethylhydroxyethyldimethylammonium, and mixtures thereof.

For example, the at least one cationic surfactant may be chosen from caprylyl trimethyl ammonium chloride (Aliquat 2); oleyl trimethyl ammonium chloride (Aliquat 11); oleyl-linoleyl trimethyl ammonium chloride (Aliquat 15); dilauryl dimethyl ammonium chloride (Aliquat 204); lauryl heterocyclic tertiary amine (Amine C); cetyl dimethyl ethyl ammonium bromide (Ammonyx DME); cetyl dimethyl benzyl ammonium chloride (Ammonyx T); lauryl trimethyl ammonium chloride (Arquad 12-50); cetyl trimethyl ammonium chloride (Arquad 16-50); stearyl trimethyl ammonium chloride (Arquad 18-50); quaternized 2-amino pentadecane (Arquad L-15); dicoco dimethyl ammonium chloride (Arquad 2C-50); N-cetyl ethyl morpholinium ethosulfate (Atlas G 263); alkenyl dimethyl ethyl ammonium bromide (Barquat OE-50); lauryl isoquinolinium bromide (Barquat IB-75); myristyl dimethyl benzyl ammonium chloride (BTC 1750); stearamido propyl dimethyl B-hydroxyethyl ammonium phosphate (Catanac SP); tetradecyl pyridinium bromide (Fixanol VR); heptadecenyl imidazolinium bromide (Intexan HB-50); quaternary substituted imidazoline of oleic acid (Monaquat OIBC); substituted imidazoline of myristic acid (Monazoline M); coco fatty dialkyl benzyl ammonium chloride (Quatrene CB); fatty glyoxalidinium chloride (Quatrene 0-56); soya fatty dialkyl benzyl ammonium chloride (Quatrene SFB); 1-hydroxyethyl 2-heptadecenyl imidazoline hydrochloride (Romine BTQ); and lauryl dimethyl benzyl ammonium chloride (Vantoc CL).

Additionally, any amphoteric molecule that can be pH adjusted to become cationic may also be chosen. Exemplary, non-limiting amphoteric surface active agents include derivatives of betaine, derivatives of alkylamphoacetates, derivatives of hydroxylsultaines, and mixtures thereof.

Non-limiting examples of betaine derivatives which may be used include cocobetaine, such as, for example, DEHYTON AB-30® from Cognis, laurylbetaine, such as GENAGEN KB® from Clariant, oxyethylenated laurylbetaine (10 OE), such as LAURYLETHER(10 OE)BETAINE® from Shin Nihon Rica, oxyethylenated stearylbetaine (10 OE), such as STEARYLETHER(10 OE)BETAINE® from Shin Nihon Rica, cocamidopropyl betaine, such as VELVETEX BK 35® from Cognis, and undecylenamidopropyl betaine, such as AMPHORAM U® from Ceca.

Exemplary and non-limiting alkylamphoacetate derivatives include N-cocoyl-N-carboxymethoxyethyl-N-carboxymethyl-ethylenediamine N-di-sodium (INCI name: disodium cocamphodiacetate), such as MIRANOL C2M CONCENTRE NP® from Rhodia Chimie, and N-cocoyl-N-hydroxyethyl-N-carboxymethyl-ethylenediamine N-sodium (INCI name: sodium cocamphoacetate).

Exemplary, non-limiting derivatives of hydroxylsultaines that may be used include Cocamidopropyl hydroxysultaine, such as that sold as REWOTERIC AM® by Golschmidt-Degussa.

Exemplary, non-limiting anionic surface active agents include mixed esters of fatty acid or of fatty alcohol, of carboxylic acid and of glycerol; alkyl ether citrates; alkenyl succinates chosen from alkoxylated alkenyl succinates, alkoxylated glucose alkenyl succinates, and alkoxylated methylglucose alkenyl succinates; and phosphoric acid fatty esters.

The mixed esters of fatty acid or of fatty alcohol, of carboxylic acid and of glycerol which can be used as anionic surface-active agents may be chosen from, by way of non-limiting example, mixed esters of fatty acid or of fatty alcohol having an alkyl chain including from 8 to 22 carbon atoms and of α-hydroxy acid and/or of succinic acid with glycerol. The α-hydroxy acid can be, for example, citric acid, lactic acid, glycolic acid, malic acid and their mixtures.

The alkyl chain of the fatty acids or alcohols from which the mixed esters which can be used can be chosen from those that are saturated or unsaturated and linear or branched. They may, by way of non-limiting example, be chosen from stearate, isostearate, linoleate, oleate, behenate, arachidonate, palmitate, myristate, laurate, caprate, isostearyl, stearyl, linoleyl, oleyl, behenyl, myristyl, lauryl and capryl chains.

Mention may be made, as examples of mixed esters which can be used as the anionic surface-active agents, of the mixed ester of glycerol and of the mixture of citric, lactic, linoleic and oleic acids (INCI name: Glyceryl citrate/lactate/linoleate/oleate) sold by Hills under the name Imwitor 375; the mixed ester of succinic acid and of isostearyl alcohol with glycerol (INCI name: Isostearyl diglyceryl succinate) sold by Huls under the name Imwitor 780 K; the mixed ester of citric acid and of stearic acid with glycerol (INCI name: Glyceryl stearate citrate) sold by Hills under the name Imwitor 370; or the mixed ester of lactic acid and of stearic acid with glycerol (INCI name: Glyceryl stearate lactate) sold by Danisco under the name Lactodan B30 or Rylo LA30.

The alkyl ether citrates which can be used as anionic surface-active agents can be chosen from, for example, the monoesters, diesters or triesters formed by citric acid and at least one oxyethylenated fatty alcohol, including a saturated or unsaturated and linear or branched alkyl chain having from 8 to 22 carbon atoms and including from 3 to 9 ethoxylated groups.

Nonlimiting examples of citrates may be chosen from the mono-, di- and triesters of citric acid and of ethoxylated lauryl alcohol, including from 3 to 9 ethoxylated groups, sold by Witco under the name Witconol EC, in particular Witconol EC 2129, which is predominantly a dilaureth-9 citrate, and Witconol EC 3129, which is predominantly a trilaureth-9 citrate.

The alkyl ether citrates that may be useful as anionic surface-active agents may, in various exemplary embodiments, be in the form neutralized to a pH of approximately 7, where the neutralizing agent may be chosen from, for example, inorganic bases, such as sodium hydroxide, potassium hydroxide, or ammonia, and organic bases such as mono-, di-, and triethanolamine, aminomethylpropane-1,3-diol, N-methyglucamine or basic amino acids, such as arginine and lysine, and their mixtures.

The alkenyl succinates which can be used as anionic surface-active agents are chosen from, for example, ethoxylated and/or propoxylated derivatives, including those of the compounds of formulae (XIV) or (XV):

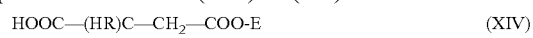

HOOC—(HR)C—CH$_2$—COO-E (XIV)

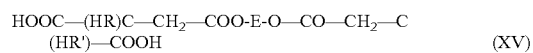

HOOC—(HR)C—CH$_2$—COO-E-O—CO—CH$_2$—C(HR')—COOH (XV)

wherein:
the R and R' radicals are chosen from linear or branched alkyl radicals including from 6 to 22 carbon atoms (including, for example, 10, 12, 14, 16, 18, and 20),
E is chosen from oxyethylene chains of formula (C2H4O)n, in which n ranges from 2 to 100 (for example 10, 20, 40, 60, 80 and 90), oxypropylene chains of formula (C3H6O)n', in which n' ranges from 2 to 100 (for example 5, 10, 20, 30, 40, 50, 60, 70, 80 and 90), random or blocked copolymers including 5 oxyethylene chains of formula (C2H4O)n and oxypropylene chains of formula (C3H6O)n', such that the sum of n and n' ranges from 2 to 100 (for example 5, 10, 20, 30, 40, 50, 60, 70, 80 and 90), oxyethylenated and/or oxypropylenated glucose groups including, on average, from 4 to 100 oxyethylene and/or oxypropylene units distributed over all the hydroxyl functional groups, or oxyethylenated and/or oxypropylenated methylglucose groups including, on average, from 4 to 100 oxyethylene and/or oxypropylene units distributed over all the hydroxyl functional groups (for example 5, 10, 20, 30, 40, 50, 60, 70, 80 and 90).

In the formulae (XIV) and (XV), n and n' are mean values and are therefore not necessarily integers. For example, n may range from 5 to 60, such as from 10 to 30.

In the formulae (XIV) and (XV), the R and/or R' radical may be chosen from linear alkyl radicals including from 8 to 22, such as from 14 to 22, carbon atoms (for example 10, 12, 14, 16, 18 and 20 carbons). It may be, for example, the hexadecenyl radical, including 16 carbon atoms, or the octadecenyl radical, including 18 carbon atoms.

The compounds of formulae (XIV) and (XV) described above in which E is chosen from oxyethylene chains, oxypropylene chains and copolymers including oxyethylene chains and oxypropylene chains can be prepared in accordance with the description in WO-A-94/00508, EP-A-1 071 99 and GB-A-2 131 820.

The acid functional group —COOH of the anionic surface-active agents of formulae (XIV) and (XV) may be neutralized by a neutralizing agent, the neutralizing agent being chosen from, for example, inorganic bases, such as sodium hydroxide, potassium hydroxide, or ammonia, and organic bases such as mono-, di-, and triethanolamine, aminomethylpropane-1,3-diol, N-methyglucamine or basic amino acids, such as arginine and lysine, and their mixtures.

Non-limiting examples of anionic surface-active agents of this type include hexadecenyl succinate 18 EO (compound of formula XIV with R=hexadecenyl, E=(C2H40)n and n=18), hexadecenyl succinate 45 EO (compound of formula XIV with R=hexadecenyl, E=(C2H40)n and n=45), dihexadecenyl succinate 18 EO (compound of formula XV with R=R'=hexadecenyl, E=(C2H40)n and n=18), dihexadecenyl succinate of glucose 10 EO (compound of formula XV with R=R'=hexadecenyl and E=oxyethylenated glucose including 10 oxyethylene groups), dihexadecenyl succinate of glucose 20 EO (compound of formula XV with R=R'=hexadecenyl and E=oxyethylenated glucose including 20 oxyethylene groups), dioctadecenyl succinate of methylglucose 20 EO (compound of formula XV with R=octadecenyl and E oxyethylenated methylglucose including 20 oxyethylene groups).

The phosphoric acid fatty esters and their oxyethylenated derivatives which can be used as anionic surface-active agents can further be chosen from esters formed of phosphoric acid and of at least one alcohol including a saturated or unsaturated and linear or branched alkyl chain having from 8 to 22 carbon atoms (for example 10, 12, 14, 16, 18 and 20) and esters formed of phosphoric acid and of at least one ethoxylated alcohol including a saturated or unsaturated and linear or branched alkyl chain having from 8 to 22 carbon atoms (for example 10, 12, 14, 16, 18 and 20) and including from 2 to 40 oxyethylene groups (for example 4, 6, 8, 10, 12, 14, 16, 18, 20 and 30), their salts and their mixtures.

These esters may, for example, be chosen from esters of phosphoric acid and of C9-C15 alcohols or their salts, such as the potassium salt of C9-15 alkyl phosphate sold under the name Arlatone MAP by ICI; esters of phosphoric acid and of stearyl and/or isostearyl alcohols, such as the phosphate of stearyl/isostearyl alcohols (INCI name: Octyldecyl phosphate) sold under the name Hostaphat CG120 by Hoechst Celanese; esters of phosphoric acid and of cetyl alcohol, and their oxyethylenated derivatives, such as the product sold under the name Crodafos CES (mixture of cetearyl alcohol, of dicetyl phosphate and of ceteth-10 phosphate) by Croda; or esters of phosphoric acid and of tridecyl alcohol, and their oxyethylenated derivatives, such as the product sold under the name Crodafos T10 (INCI name: Trideceth-10 phosphate) by Croda. The oxyethylenated derivatives of phosphoric acid and of fatty alcohol can be prepared in accordance with the description given in WO-A-96/14145, for example.

Additional non-limiting examples of anionic surface-active agents that may be used include alkaline salts of dicetyl and dimyristyl phosphate, alkaline salts of cholesterol sulfate, alkaline salts of cholesterol phosphate, lipoamino acids and their salts, such as mono- and disodium acylglutamates, for instance the disodium salt of N-stearoyl-L-glutamic acid sold under the name Acylglutamate HS21 by Ajinomoto, sodium salts of phosphatidic acid, phospholipids, alkylsulfonic derivatives, such as those of formula (XVI):

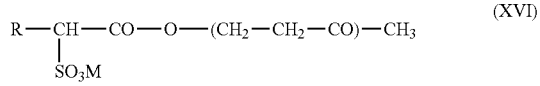

(XVI)

wherein:
R represents C16-C22 alkyl radicals, for example the C16H33 and C18H37 radicals taken as a mixture or separately, and
M is an alkali metal or an alkaline earth metal, such as sodium.

It should also be noted that mixtures of cationic surface-active agents may be used in certain exemplary embodiments. In further exemplary embodiments, mixtures of anionic surface-active agents may be used.

The continuous phase may optionally further comprise any additional component that may be desired in the final emulsion, depending on the ultimate intended application. By way of non-limiting example only, the continuous phase may optionally further comprise at least one humectant, sugar, polymer, peptide, UV absorber, sunscreen, dye, etc. In yet further exemplary embodiments, the continuous phase may comprise lipophilic active agents or lipophilic active compounds: retinol (vitamin A) and derivatives thereof, tocopherol (vitamin E) and derivatives thereof, essential oils or unsaponifiable materials (e.g., bergamot, tocotrienol, sesamine, gamma-oryzanol, phytosterols, squalenes, waxes and terpenes), ascorbyl palmitate, vitamin F glycerides, D vitamins, vitamin D2, vitamin D3, retinol, retinol esters, retinyl palmitate, retinyl propionate, carotenes including beta-carotene, D-panthenol, farnesol, farnesyl acetate, salicylic acid and compounds thereof, for instance 5-n-octanoylsalicylic acid, alkyl esters of alpha-hydroxy acids such as citric acid, lactic acid, glycolic acid, asiatic acid, madecassic acid, asiaticoside, the total extract of *Centella asiatica*, beta-glycyrrhetinic acid, alpha-bisabolol, ceramides, for instance 2-oleoylamino-1,3-octadecane, phytanetriol, phospholipids of marine origin rich in polyunsaturated essential fatty acids, ethoxyquine, rosemary extract, balm extract, quercetin, extract of dried microalgae, octyl methoxycinnamate, butylmethoxydibenzoylmethane, octyl triazone, 3,5-di-tert-butyl-4-hydroxy-3-benzylidenecamphor, antibiotics, antifungal agents, anaesthetics, analgesics, antiseptics, antiviral agents, pesticides and herbicides, and mixtures thereof. One of skill in the art will be able to select both the type and amount of optional additional component in order to avoid degradation of the emulsion.

For example, in at least certain embodiments, the continuous phase may optionally comprise at least one lipophilic active agent or compounds. Non-limiting examples include retinol (vitamin A) and derivatives thereof, tocopherol (vitamin E) and derivatives thereof, essential oils or unsaponifiable materials (e.g., bergamot, tocotrienol, sesamine, gamma-oryzanol, phytosterols, squalenes, waxes and terpenes), ascorbyl palmitate, vitamin F glycerides, D vitamins, vitamin D2, vitamin D3, retinol, retinol esters, retinyl palmitate, retinyl propionate, carotenes including beta-carotene, D-panthenol, farnesol, farnesyl acetate, salicylic acid and compounds thereof, for instance 5-n-octanoylsalicylic acid, alkyl esters of alpha-hydroxy acids such as citric acid, lactic acid, glycolic acid, asiatic acid, madecassic acid, asiaticoside, the total extract of *Centella asiatica*, beta-glycyrrhetinic acid, alpha-bisabolol, ceramides, for instance 2-oleoylamino-1,3-octadecane, phytanetriol, phospholipids of marine origin rich in polyunsaturated essential fatty acids, ethoxyquine, rosemary extract, balm extract, quercetin, extract of dried microalgae, octyl methoxycinnamate, butylmethoxydibenzoylmethane, octyl triazone, 3,5-di-tert-butyl-4-hydroxy-3-benzylidenecamphor, antibiotics, antifungal agents, anaesthetics, analgesics, antiseptics, antiviral agents, pesticides and herbicides, and mixtures thereof.

Separately, a solution of particles can be prepared. The solution may optionally be an aqueous solution, and may comprise particles that have a charge opposite to that of the charge on the coated bubble. The particles may have a contact angle of less than about 90°, such as less than about 75°, less than about 50°, or less than about 25°.

The particles may be present in the solution in a concentration ranging up to about 35 wt %, such as up to about 25 wt %, up to about 20 wt %, up to about 15 wt %, up to about 10 wt %, or up to about 5 wt %. For example, the particles may be present in a concentration ranging from about 0.10 wt % to about 30 wt %, about 0.25 wt % to about 25 wt %, about 0.50 wt % to about 20 wt %, or about 1 wt % to about 10 wt %.

The charge on the particle may be, for example, greater than about 15 mV, such as greater than about 20 mV, greater than about 25 mV, greater than about 30 mV, greater than about 35 mV, greater than about 40 mV, greater than about 45 mV, or greater than about 50 mV.

The particles may be chosen from particles of any shape, including, but not limited to, those that are substantially spherical, platelet-shaped, elongated, feather-shaped, and fiber-shaped, including mixtures thereof.

The average diameter of spherical particles may range, for example, up to about 20 µm, such as up to about 10 µm, up to about 5 µm, up to about 2 µm, or up to about 1 µm. By way of example, the diameter of spherical particles may range from about 10 nm to about 10 µm, such as about 25 nm to about 10 µm, about 50 nm to about 10 µm, about 100 nm to about 10 µm, about 500 nm to about 10 µm, about 1 µm to about 10 µm, about 10 nm to about 5 µm, about 25 nm to about 5 µm, about 50 nm to about 5 µm, about 100 nm to about 5 µm, about 500 nm to about 5 µm, about 1 µm to about 5 µm, about 10 nm to about 20 µm, about 25 nm to about 2 µm, about 50 nm to about 2 µm, about 100 nm to about 2 µm, about 500 nm to about 2 µm, or about 1 µm to about 2 µm. Spherical particles may have a form factor (aspect ratio) ranging from about 1 to about 2.

The particles that are platelet-shaped may have a width and/or length ranging, independently, up to about 1000 µm, such as up to about 750 µm, up to about 500 µm, up to about 250 µm, up to about 100 µm, or up to about 50 µm. For example, the width and/or diameter may range from about 1 µm to about 750 µm, such as about 1 µm to about 500 µm, or about 1 µm to about 250 µm. The thickness of the platelet-shaped particles may range up to about 5 µm, such as up to about 2 µm, or up to about 1 µm. For example, the thickness may range from about 100 nm to about 5 µm, such as about 100 nm to about 2 µm, or about 100 to about 1 µm.

The particles that are fiber-shaped may have a length ranging up to about 100 µm, such as up to about 50 µm, up to about 25 µm, or up to about 15 µm. For example, the length may range from about 0.5 µm to about 100 µm, such as 0.5 µm to about 50 µm. The diameter of the fiber-shaped particles may range up to about 750 nm, such as up to about 500 nm, up to about 250 nm, or up to about 100 nm. For example, the diameter may range from about 1 nm to about 750 nm, such as about 5 nm to about 500 nm, about 10 nm to about 250 nm, or about 25 nm to about 100 nm.

Particles useful according to various embodiments of the disclosure may be chosen from organic or inorganic particles, optionally surface-modified to provide electrostatic interaction with the surface-active agent. For example, particles may be chosen from nylon particles, PPMA particles, styrene particles, and silica particles. One of skill in the art will understand that any particles which have an electrostatic interaction with the surface-active agent may be chosen.

It may, in at least certain embodiments, be desirable to choose the gas bubble and particle sizes such that the bubble to particle size ratio ranges from about 1 to about 25, such as about 5 to about 20, about 7.5 to about 15, or about 10.

After the particle solution is prepared, the solution may be mixed with the gas-in-solution dispersion in a desired ratio. For example, the ratio of particle solution:gas-in-solution dispersion may range from about 20:80 to about 80:20, such as about 40:60 to about 60:40, or about 50:50.

Methods for preparing encapsulated gas bubbles, and emulsions comprising encapsulated gas bubbles, according to embodiments of the disclosure may be useful for preparing gas-in-solution emulsions for use in a variety of industries, such as, by way of non-limiting example, food, personal care (e.g. cosmetic, dermatological, perfume, etc.), pharmaceutical, and consumer chemical (e.g. household products). It may also be possible to incorporate gas-in-solution emulsions prepared according to embodiments of the disclosure into compositions or emulsions (e.g. O/W, W/O, W/O/W, etc.) for use in a variety of industries, such as, by way of non-limiting example, food, personal care (e.g. cosmetic, dermatological, perfume, etc.), pharmaceutical, and consumer chemical (e.g. household products). As such, compositions, emulsions, and products comprising gas-in-solution emulsions according to embodiments of the disclosure, or comprising gas bubbles encapsulated according to embodiments of the disclosure, are further intended to be within the scope of the disclosure.

In at least certain exemplary embodiments according to the disclosure, the compositions, emulsions, and products comprising bubbles encapsulated according to various embodiments of the disclosure may be stable for a period of several months, such as up to about 24 months, up to about 18 months, up to about 12 months, or up to about 6 months, at room temperature. It should be noted, however, that stability may vary according to various embodiments of the disclosure, and/or compositions, emulsions, and/or products made according to embodiments described herein may not offer improved stability over an extended period of time, yet such embodiments are intended to be within the scope of the disclosure.

As described herein, steps of various processes and procedures are listed in a certain order. However, it is to be understood that, unless explicitly stated otherwise, the order of performing the steps in the processes or procedures is not critical, and thus, processes and procedures having the specified steps, but in a different order, are likewise intended to be within the scope of the disclosure.

Unless otherwise indicated, all numbers used in the specification and claims are to be understood as being modified in all instances by the term "about," whether or not so stated. It should also be understood that the precise numerical values used in the specification and claims form additional embodiments of the invention, and are intended to include any ranges which can be narrowed to any two end points disclosed within the exemplary ranges and values provided. Efforts have been made to ensure the accuracy of the numerical values disclosed herein. Any measured numerical value, however, can inherently contain certain errors resulting from the standard deviation found in its respective measuring technique.

All patents and published applications mentioned herein are incorporated by reference in their entireties.

EXAMPLE

The following Example is intended to be non-restrictive and explanatory only, with the scope of the invention being defined by the claims.

Example

An aqueous solution of hydroxy trimethyl ammonium chloride surfactant was prepared having 3 times the CMC, at neutral pH. Air bubbles were mixed with the aqueous solution to generate a gas-in-solution dispersion.

Next, a 5 wt % particle solution was prepared using silica particles. The pH of the solution was adjusted to greater than 7, using HCl 23 wt % and NaOH 1M solutions.

The gas-in-water emulsion and particle solution were mixed 50:50 by volume to prepare a gas-in-water emulsion having tightly encapsulated bubbles. The dispersion was kept at pH 6 at room temperature (23° C., ±5° C.) for over two years, and remained stable.

Figure 4:
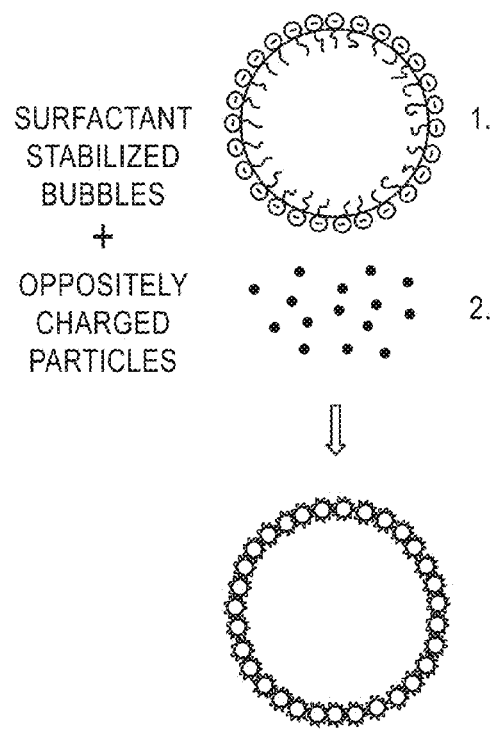
FIG. 4 is a schematic of a process for encapsulating gas bubbles, according to an exemplary embodiment of the disclosure.
Figure 5:
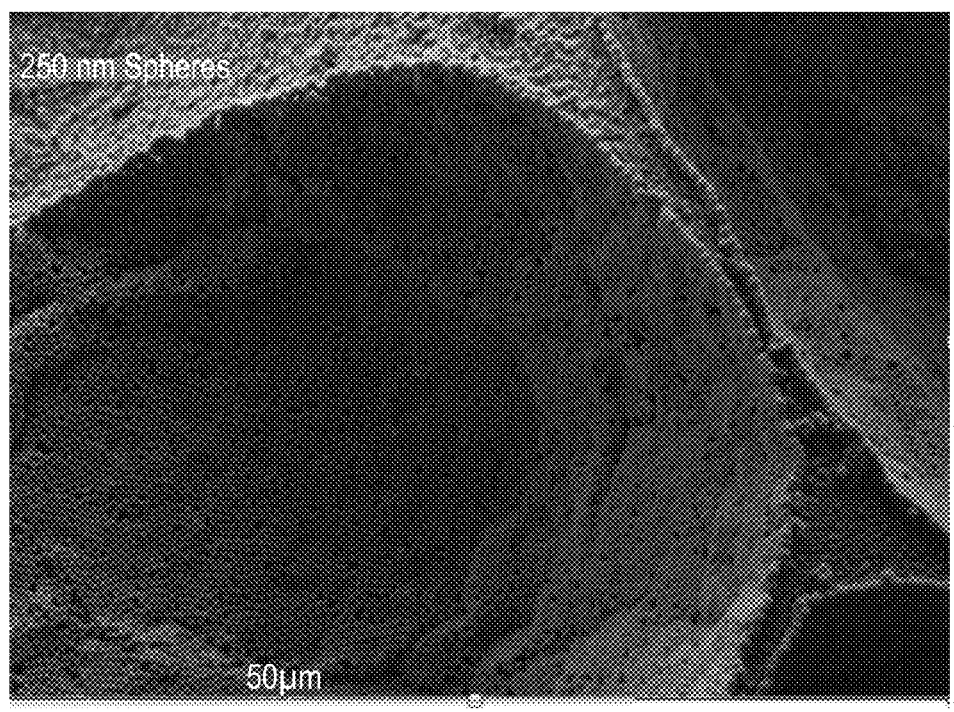
FIG. 5 is an SEM image of spherical particles tightly covering the surface of a gas bubble encapsulated according to an exemplary embodiment of the disclosure.
Figure 6:
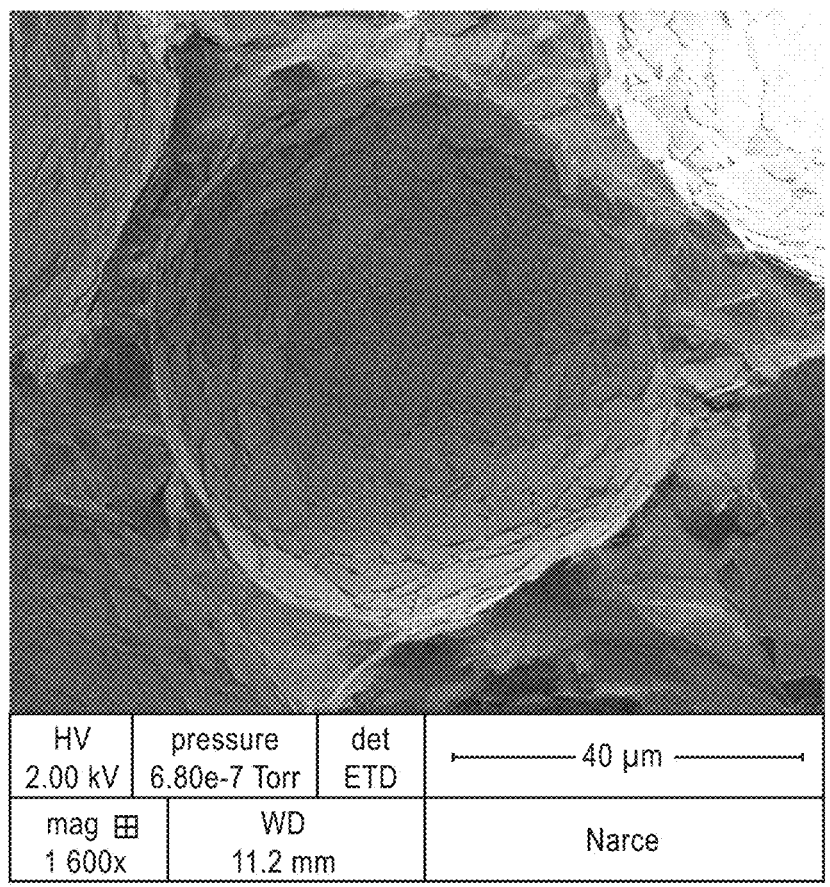
FIG. 6 is an SEM image of a gas bubble with platelets tightly covering the surface, prepared according to an exemplary embodiment of the disclosure.

An exemplary schematic is seen in FIG. 4.

What is claimed is:

1. A method for preparing an emulsion, said method comprising mixing a gas-in-solution dispersion and a solution comprising particles, wherein:
   a. the gas-in-solution dispersion comprises at least one surface active agent in the continuous phase, and a disperse phase comprising gas bubbles; and
   b. the particle solution comprises particles having an opposite charge than that of the surface active agent.

2. The method according to claim 1, wherein the gas bubbles are chosen from bubbles of air, $O_2$, $N_2$, $CO_2$, $N_2O$, He, and combinations thereof.

3. The method according to claim 1, wherein the at least one surface active agent is chosen from cationic and anionic surface active agents.

4. The method according to claim 3, wherein the at least one cationic surface active agent is chosen from optionally polyoxyalkylenated primary, secondary and tertiary fatty amines, quaternary ammonium salts, and mixtures thereof.

5. The method according to claim 3, wherein the at least one cationic surface active agent is chosen from at least one amphoteric surface active agent that has been pH-adjusted to be cationic.

6. The method according to claim 5, wherein the at least one cationic surface active agent chosen from at least one amphoteric surface active agent that has been pH-adjusted to be cationic is chosen from derivatives of betaine, derivatives of alkylamphoacetate, derivatives of hydroxylsultaines, and mixtures thereof.

7. The method according to claim 3, wherein the at least one anionic surface active agent is chosen from alkyl ether citrates; alkenyl succinates chosen from alkoxylated alkenyl succinates, alkoxylated glucose alkenyl succinates, and alkoxylated methylglucose alkenyl succinates; phosphoric acid fatty esters; alkaline salts of dicetyl and dimyristyl phosphate; alkaline salts of cholesterol sulfate; alkaline salts of cholesterol phosphate; lipoamino acids and their salts; sodium salts of phosphatidic acid; phospholipids; alkylsulfonic derivatives; and mixed esters of glycerol with 1) and 2), wherein 1) and 2) are as follows: 1) at least one fatty acid or fatty alcohol, and 2) at least one carboxylic acid.

8. The method according to claim 1, wherein the gas bubbles have a charge greater than about 40 mV after preparing the gas-in-solution dispersion.

9. The method according to claim 8, wherein the particles have a charge greater than about 20 mV after preparing the particle solution.

10. The method according to claim 1, wherein the particles are chosen from organic and inorganic particles.

11. The method according to claim 10, wherein the particles are surface-modified to provide electrostatic interaction with the surface-active agent.

12. The method according to claim 10, wherein the particles are chosen from nylon particles, PPMA particles, styrene particles, and silica particles.

13. The method according to claim 1, wherein the gas bubble to particle size ratio ranges from about 5 to about 20.

14. The method according to claim 1, wherein the solution comprising particles comprises particles having a contact angle of less than about 90°.

15. The method according to claim 1, wherein the particles are present in the solution in an amount ranging from about 0.2 wt % to about 25 wt %.

16. A method for preparing an emulsion, said method comprising the steps of:
   a. preparing a solution having at least one cationic surface active agent;
   b. dispersing gas bubbles in the solution to obtain a gas-in-solution dispersion comprising gas bubbles having a cationic charge;
   c. preparing a solution comprising particles having an anionic charge; and
   d. mixing the gas-in-solution dispersion comprising gas bubbles having a cationic charge and the solution comprising particles having an anionic charge.

17. A method for preparing an emulsion, said method comprising the steps of:
   a. preparing a solution having at least one anionic surface active agent;
   b. dispersing gas bubbles in the solution to obtain a gas-in-solution dispersion comprising gas bubbles having an anionic charge;
   c. preparing a solution comprising particles having a cationic charge; and
   d. mixing the gas-in-solution dispersion comprising gas bubbles having an anionic charge and the solution comprising particles having a cationic charge.

18. A gas-in-solution emulsion comprising gas bubbles comprising a cationic charge at the gas/solution interface, wherein said gas bubbles are encapsulated by anionic particles.

19. A gas-in-solution emulsion comprising gas bubbles comprising an anionic charge at the gas/solution interface, wherein said gas bubbles are encapsulated by cationic particles.

20. The gas-in-solution emulsion according to claim 18, wherein the emulsion is stable for at least 6 months at room temperature.

21. The gas-in-solution emulsion according to claim 19, wherein the emulsion is stable for at least 6 months at room temperature.

\* \* \* \* \*